US008491692B2

(12) United States Patent
Anderson et al.

(10) Patent No.: US 8,491,692 B2
(45) Date of Patent: Jul. 23, 2013

(54) DISPERSABLE POTASH GRANULE

(75) Inventors: Charles W. Anderson, Bowling Green, OH (US); Timothy D. Birthisel, Perrysburg, OH (US)

(73) Assignee: The Andersons, Inc., Maumee, OH (US)

( * ) Notice: Subject to any disclaimer, the term of this patent is extended or adjusted under 35 U.S.C. 154(b) by 0 days.

(21) Appl. No.: 12/876,536

(22) Filed: Sep. 7, 2010

(65) Prior Publication Data

US 2011/0218102 A1 Sep. 8, 2011

Related U.S. Application Data

(63) Continuation-in-part of application No. 11/672,553, filed on Feb. 8, 2007, now Pat. No. 7,789,932.

(60) Provisional application No. 60/771,408, filed on Feb. 8, 2006, provisional application No. 60/790,345, filed on Apr. 7, 2006.

(51) Int. Cl.
  *C05F 5/00* (2006.01)
  *C05F 7/00* (2006.01)
  *C05F 11/00* (2006.01)
  *C05F 11/10* (2006.01)
  *C05F 1/00* (2006.01)
  *C05F 3/00* (2006.01)
  *C05F 3/02* (2006.01)

(52) U.S. Cl.
  USPC ............... 71/8; 71/11; 71/15; 71/17; 71/18; 71/21; 71/23; 71/24; 71/25; 71/28; 71/29; 71/30; 71/48; 71/50; 71/51; 71/53; 71/58; 71/59; 71/60; 71/63; 71/903; 504/101; 504/102

(58) Field of Classification Search
  USPC ............... 71/11–30, 8, 903, 48, 50, 51, 53, 71/58, 59, 60, 63; 504/101, 102
  See application file for complete search history.

(56) References Cited

U.S. PATENT DOCUMENTS

| | | | |
|---|---|---|---|
| 3,725,029 A | 4/1973 | Blackmore | |
| 4,304,589 A | 12/1981 | Kamo et al. | |
| 4,378,238 A | 3/1983 | Goertz | |
| 4,394,149 A | 7/1983 | Szoka, Jr. et al. | |
| 4,789,391 A | 12/1988 | Detroit | |
| 4,846,871 A | 7/1989 | Detroit | |
| 5,041,153 A | 8/1991 | Detroit | |
| 5,075,402 A | 12/1991 | Schmitt et al. | |
| 5,114,458 A | 5/1992 | Castillo et al. | |
| 5,238,480 A | 8/1993 | Rehberg et al. | |
| 5,286,272 A | 2/1994 | Biamonte et al. | |
| 5,328,497 A | 7/1994 | Hazlett | |
| 5,344,871 A * | 9/1994 | Timm et al. ............ | 525/54.3 |
| 5,354,742 A | 10/1994 | Deming et al. | |
| 5,360,465 A | 11/1994 | Buchholz et al. | |
| 5,433,766 A | 7/1995 | Ming et al. | |
| 5,451,242 A | 9/1995 | Ming et al. | |
| 5,629,261 A | 5/1997 | Narayanan et al. | |
| 5,714,157 A | 2/1998 | Sandell et al. | |
| 5,739,081 A | 4/1998 | Lloyd et al. | |
| 5,976,210 A | 11/1999 | Sensibaugh | |
| 6,013,209 A | 1/2000 | Phinney | |
| 6,030,565 A | 2/2000 | Golan | |
| 6,101,763 A | 8/2000 | Aoki et al. | |
| 6,132,484 A | 10/2000 | Phinney | |
| 6,287,496 B1 * | 9/2001 | Lownds ............ | 264/118 |
| 6,293,985 B1 | 9/2001 | Phinney | |
| 6,299,663 B1 | 10/2001 | Phinney | |
| 6,406,510 B1 * | 6/2002 | Burnham ............ | 71/11 |
| 6,454,979 B1 | 9/2002 | Phinney | |
| 6,464,746 B2 | 10/2002 | Neyman et al. | |
| 6,582,637 B1 | 6/2003 | Phinney | |
| 6,884,756 B2 | 4/2005 | Lynch et al. | |
| 6,936,087 B2 * | 8/2005 | Wommack et al. ....... | 71/19 |
| 7,468,087 B2 | 12/2008 | Sakamoto et al. | |
| 7,666,399 B2 | 2/2010 | Birthisel et al. | |
| 7,789,932 B2 | 9/2010 | Anderson et al. | |
| 7,850,758 B2 | 12/2010 | Birthisel et al. | |
| 7,867,507 B2 | 1/2011 | Birthisel et al. | |
| 2002/0011087 A1 | 1/2002 | Neyman et al. | |
| 2004/0065127 A1 * | 4/2004 | Connell ............ | 71/15 |
| 2005/0217332 A1 * | 10/2005 | Keller et al. ............ | 71/11 |
| 2005/0241354 A1 | 11/2005 | Wommack et al. | |
| 2007/0062232 A1 * | 3/2007 | Urano et al. ............ | 71/11 |
| 2007/0131010 A1 | 6/2007 | Binder et al. ............ | 71/23 |
| 2010/0064747 A1 * | 3/2010 | Greer et al. ............ | 71/11 |
| 2010/0139346 A1 * | 6/2010 | Burnham ............ | 71/12 |
| 2010/0326151 A1 * | 12/2010 | Madigan et al. ............ | 71/8 |

* cited by examiner

*Primary Examiner* — Wayne Langel

(74) *Attorney, Agent, or Firm* — Blue Filament Law PLLC; Avery N. Goldstein; Marc S. Balban

(57) ABSTRACT

A water-dispersible particle is provided that includes organic origin potash in an amount ranging from 5% to 99.9% by weight of the total dry weight of the particle. A binder component is present in an amount from 1% to 95% by weight. The organic origin potash and the binder component on that contact with water causes particle dispersion into more than 100 pieces.

A process for making a water-dispersible particle includes mechanical aggregation of the potash into a pellet. A binder component is present in the particle in an amount ranging from 1% to 95% by weight. The potash and the binder component are present in a form such that contact with water causes particle dispersion into more than 100 pieces. The pellet is then dried and ready to be applied.

17 Claims, No Drawings

DISPERSABLE POTASH GRANULE

CROSS-REFERENCE TO RELATED APPLICATIONS

This application is a continuation-in-part of U.S. utility application Ser. No. 11/672,553 filed 8 Feb. 2007; which in turn claims priority of U.S. Provisional Patent Application Ser. No. 60/790,345 filed Apr. 7, 2006 and U.S. Provisional Patent Application Ser. No. 60/771,408 filed Feb. 8, 2006, which are incorporated herein by reference.

FIELD OF THE INVENTION

The present invention relates to water-dispersible potash. More particularly, the present invention relates to water-dispersible potash of organic origin.

DESCRIPTION OF THE RELATED ART

A continuing problem in care of large areas of cultivated vegetation is the difficulty of delivery of fertilizer to the target in an efficient manner. A practical and labor-saving approach to agent delivery in areas such as golf courses, parks, lawns, gardens and woodlands has been broadcast application of granular products containing an agent, for example via rotary spreader. Using granular products having particle sizes in the range of about 1 millimeter to about 10 millimeters, an operator can cover a large area with minimal distance traversed by the spreader itself, while applying the granular products relatively uniformly to the desired area. Unfortunately, such granular products often remain in solid or semisolid form several days following their application yielding a high concentration dispersion zone immediately beneath a particle with much lower concentrations in proximity. With potash delivery this can lead to chemical burning proximal to a pellet.

A further consequence of the fact that granular products often remain in solid or semisolid form for long periods following application is that the granules are subject to removal by cultural practices such as mowing with clipping removal, leaf and or yard waste vacuuming; or runoff from weather events, especially on sloping ground where the underlying soils have low percolation rates; where the ground cover is closely mown or relatively thin and sparse; and where the equipment or pedestrian traffic is high. This causes a loss of the uniformity of the biological response sought by the use of the product. In addition, product efficacy may be altered due to excessive concentration of the product within the areas treated.

The long persistence of the granular products also results in a greater likelihood that people and or animals may come into physical contact with the granules, which may result in skin irritation, sensitization, dermal absorption and toxicity. Additionally, when clothing, footwear and equipment come into physical contact with the granules, they can cause damage, corrosion or staining.

The present invention solves the problems associated with persistence of granular products by providing compositions and methods for making controlled release nitrogen pellets that are water dispersible. The inventive pellets, when handled without coming into contact with water, have physical characteristics similar to existing controlled release granules such as those detailed in U.S. Pat. No. 6,884,756. Following application, the inventive pellets disperse on contact with moisture from the treated area itself, from irrigation or from natural precipitation. The dispersion of the pellets allows the controlled release nitrogen and other active ingredients to be deposited downwards and laterally from the original position of the pellet, so that the controlled release nitrogen and other active ingredients are less likely to be removed from the treated area, ingested by small children or animals, or otherwise contacted by people, animals, clothing, footwear or equipment. Water dispersibility also prevents wastage of any relatively expensive components of the inventive pellets since more of the ingredients reach their respective targets.

While mineral mined sources of potash have predominantly supplied the agricultural and horticultural needs for potash mineral, there is a growing recognition that traditional biological sources of potassium may reduce the ecological footprint of potash material production. Additionally, biological sources of potassium often lend themselves to pelletizing.

Thus, there is a continuing need for a uniformly sized, durable product in particle form which can deliver potash in a controlled release manner and whose components are quickly dispersible in order to provide even delivery of active agents to target plants and organisms over a large area. There further exists a need to produce such a pellet from biological sources of potassium.

SUMMARY OF THE INVENTION

A water-dispersible particle is proving that includes a potassium source of organic origin present in an amount ranging from 5% to 99.9% by weight of the total dry weight of the particle. A potassium source of organic origin is synonymously referred to herein as organic potash. A binder component is present in an amount ranging from 1% to 95% by weight of the total dry weight of the particle. The potassium source of organic origin and the binder component are present in a form such that contact with water causes particle dispersion into more than 100 pieces.

A process for making a water-dispersible particle includes mechanical aggregation of a potassium source of organic origin into a pellet. A binder component, is present in the particle in an amount ranging from 1% to 95% by weight of the total dry weight of the particle. The potassium source of organic origin and the binder component are present in a form such that contact with water causes particle dispersion into more than 100 pieces. The pellet is then dried and ready to be applied.

DETAILED DESCRIPTION OF THE PREFERRED EMBODIMENTS

The present invention relates to a water-dispersible potash particle for delivery of fertilizer to a plant. The invention further relates to a method for making and using the water-dispersible particle. The inventive particle retains its size and shape during handling and application to a desired area and dissolves or crumbles into small particles upon contact with a water overspray within twelve hours. Thus the durability of the particle allows delivery of the particle to the vicinity of the desired site of action whereupon contact with water sufficient to wet the particle surface causes dispersion of particle components, facilitating distribution of the active agents to the target. The term dispersion in the context of the present invention is intended to mean that an inventive particle disperses by breaking into numerous smaller pieces upon contact with water. In a preferred embodiment, an inventive particle disperses by breaking up into greater than 100 smaller pieces upon contact with water over a period of time ranging from 1 second to 24 hours. Preferably, an inventive particle disperses into 1,000 to 10,000 smaller pieces over a period of time ranging from 1 second to 12 hours. Even more preferably, a particle disperses into 100 to 10,000 smaller pieces over a period of 30 seconds to 6 hours. Most preferably, a particle disperses as described over a period of 1 minute to 1 hour. The ability of the inventive material to degrade with water is generally measured in a water dispersibility test. The test involves placing about 10 grams of the inventive material into 100 ml of water at room temperature in a closed glass container. The container is then inverted and the time is observed until the material disperses. After every minute, the container is inverted. The inventive material of the present invention has a dispersibility time of generally less than 15 minutes with a period of less than 5 minutes being preferred and a period of less than 2 minutes being most preferred. The inventive particle provides a delivery system for potash, and optional additional agents such as nitrogen sources, plant nutrients, pesticides, hormones, herbicides, micronutrients and other active ingredients.

Composition of Particles

A particle of the present invention has a potassium source of organic origin and a binder component. Organic sources of potassium ions or organic potash include manure; kali vinesse; seaweed; cellulosic products such as saw dust, bark, chips, grain hulls, sillage; and ashes formed from any of the above. The particle optionally contains an active ingredient. In a preferred embodiment the water-dispersible potash is targeted to cultivated plants such as lawn grass, crops, flowers, shrubs, trees and bushes. The water-dispersible potash is present in amounts ranging from 5% to 99.9% by weight of the total dry weight of the particle. More preferably, the water-dispersible potash is present in amounts ranging from 30% to 99.5% by weight of the total dry weight of the particle. Still more preferably, the water-dispersible potash is present in amounts ranging from 50% to 99% by weight of the total dry weight of the particle.

An optional nitrogen-containing ingredient added to the water-dispersible potash includes methylene urea oligomers, oxamide, urea formaldehyde-based compounds, dicyandiamide, crotilidiene diurea, nitrocellulose, metal ammonium phosphates, ammonium nitrate, ammonium sulfate, urea, coated urea, monoammonium phosphate, diammonium phosphate, calcium nitrate, isobutylidene diurea and other fertilizers as detailed herein.

In a preferred embodiment the particle contains a binder that produces or promotes cohesion of the organic potash water-dispersible fine particles. The binder component is present in amounts ranging from 1% to 95% by weight of the total dry weight of the particle. More preferably, the binder component is present in amounts ranging from 1% to 75% by weight of the total dry weight of the particle. Still more preferably, the binder component is present in amounts ranging from 1% to 50% by weight of the total dry weight of the particle. Most preferably, the binder is present in amounts ranging from 1% to 25% by weight of the total dry weight of the particle. Illustrative examples of binders operative herein are carbohydrates such as monosaccharides, disaccharides, oligosaccharides and polysaccharides; proteins; lipids; glycolipid; glycoprotein; lipoprotein; clays; and combinations and derivatives of these. Specific carbohydrate binders illustratively include glucose, mannose, fructose, galactose, sucrose, lactose, maltose, xylose, arabinose, trehalose and mixtures thereof such as corn syrup; celluloses such as carboxymethylcellulose, ethylcellulose, hydroxyethylcellulose, hydroxy-methylethylcellulose, hydroxyethylpropyl cellulose, methylhydroxyethyl-cellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; complex organic substances such as lignin and nitrolignin; derivatives of lignin such as lignosulfonate salts illustratively including calcium lignosulfonate and sodium lignosulfonate and complex carbohydrate-based compositions containing organic and inorganic ingredients such as molasses. Suitable protein binders illustratively include soy extract, zein, protamine, collagen, and casein. Binders operative herein also include synthetic organic polymers capable of promoting or producing cohesion of methylene urea oligomer fines and these illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex. Clay binders illustratively include montmorillonite, and bentonite.

The particles of the present invention are optionally associated with an active ingredient. Illustrative examples of active ingredients include fertilizers, soil nutrients, amendment materials, biological factors and biostimulants. A solid, liquid or powder active ingredient is recognized to be operative herein. It will be recognized by those skilled in the art that more than one active ingredient may be incorporated into the particle and that the choice of active ingredient or combination of active ingredients will depend on the intended purpose of the particle and the chemical compatibility of the ingredients and other particle components.

In a preferred embodiment, where the active ingredient is a fertilizer, soil nutrient or amendment material, the fertilizer, soil nutrient or amendment material active ingredient is present in an amount ranging from 0.05% to 50% by weight of the total dry weight of the particle. In a more preferred embodiment, the fertilizer, soil nutrient or amendment material active ingredient is present in an amount ranging from 0.1% to 30% by weight of the total dry weight of the particle. In a still more preferred embodiment, the fertilizer, soil nutrient or amendment material active ingredient is present in an amount ranging from 0.5% to 10% by weight of the total dry weight of the particle.

Where the active ingredient is a biological factor or biostimulant, the active ingredient is present in an amount ranging from 0.05% to 10% by weight of the total dry weight of the particle. In a more preferred embodiment, the biological factor or biostimulant active ingredient is present in an amount ranging from 0.1% to 5% by weight of the total dry weight of the particle. In a still more preferred embodiment, the biological factor or biostimulant active ingredient is present in an amount ranging from 0.25% to 1% by weight of the total dry weight of the particle.

Fertilizers are substances containing one of the plant nutrients nitrogen, phosphate or potassium and illustratively include urea, sulfur-coated urea, isobutylidene diurea, ammonium nitrate, ammonium sulfate, ammonium phosphate, triple super phosphate, phosphoric acid, potassium sulphate, potassium nitrate, potassium metaphosphate, potassium chloride, dipotassium carbonate, potassium oxide and a combination of these. Soil nutrients illustratively include calcium, magnesium, sulfur, iron, manganese, copper, zinc; oxides thereof, salts thereof and combinations thereof. Amendment materials are natural organic products such as humic acid, blood meal, bone meal, seed meal, feather meal and soy meal; meat meal; animal waste from various animal sources; activated sludge, hydrolyzed animal hair; fish byproducts; chitin; composts; and a combination thereof. Biological factors are those factors that have a deleterious effect on a biological organism and illustratively include algicides, bacteriocides, defoliants, desiccants, fungicides, herbicides, insecticides, insect growth regulators, miticides, nematicides, ovicides, pesticides, pheromones, repellents, rodenticides and a combination thereof. Biostimulants are substances that promote plant survival and health and illustratively include plant growth hormones and plant growth regulators such as cytokinins, auxins, gibberellins, ethylene, absisic acid and a combination of these.

Method of Making Particles

In a preferred embodiment, water-dispersible potash fines are mechanically aggregated into pellets in a pan-granulator in the presence of a binder. Water-dispersible potash fines are small methylene urea oligomer aggregates that have a mean aggregate domain size that is less than 500 micrometers. More preferably, the mean aggregate domain size of the fines is less than 250 micrometers. Still more preferably, the mean aggregate domain size of the fines is less than 180 micrometers.

The binder is sprayed into the pan granulator with the water-dispersible potash fines. The pellets are dried and the resulting particles are size-screened and particles of desired size are stored. Optionally, the particles are transferred to a coating drum for addition of an active ingredient or a conditioner material.

In another embodiment, methylene urea oligomer fines are mechanically aggregated into pellets in a drum-granulator in the presence of a binder. Water-dispersible potash fines are small methylene urea oligomer aggregates that have a mean aggregate domain size that is less than 500 micrometers. More preferably, the mean aggregate domain size of the fines is less than 250 micrometers. Still more preferably, the mean aggregate domain size of the fines is less than 180 micrometers.

The binder is sprayed into the drum granulator with the water-dispersible potash fines. The pellets are dried and the resulting particles are size-screened and particles of desired size are stored. Optionally, the particles are transferred to a coating drum for addition of an active ingredient or a conditioner material.

In another embodiment, water-dispersible potash fines are mechanically aggregated into pellets in an Eirich unit in the presence of a binder. Water-dispersible potash fines are small methylene urea oligomer aggregates that have a mean aggregate domain size that is less than 500 micrometers. More preferably, the mean aggregate domain size of the fines is less than 250 micrometers. Still more preferably, the mean aggregate domain size of the fines is less than 180 micrometers.

The binder is sprayed into the Eirich unit granulator with the water-dispersible potash fines. The pellets are dried and the resulting particles are size-screened and particles of desired size are stored. Optionally, the particles are transferred to a coating drum for addition of an active ingredient or a conditioner material.

Various means of drying the material are available. A preferred method is fluid bed drying. The material is placed in a fluid bed drier and the drier inlet air temperature ranges from about 120° F. to about 220° F. More preferably, the temperature ranges from 140° F. to 190° F. Further methods of drying particles will be apparent to one of skill in the art and illustratively include use of a rotary drum drier and drying under vacuum conditions.

Association of an Active Ingredient with a Particle

An active ingredient is associated with a particle during the process of particle formation or after particles are formed. For example, an active ingredient is mixed with the binder. The binder/active ingredient mixture is added to water-dispersible potash fines and mechanically aggregated in a pan granulator resulting in particles wherein the active ingredient and water-dispersible potash are in suspension in the binder.

Where it is desirable to add the active ingredient after particle formation, for example where the active ingredient is incompatible with suspension in the binder, the active ingredient is added to the particle following particle formation in the presence or absence of an adhesive. Methods of active ingredient addition illustratively include spraying onto the particle or adsorption of the active ingredient by coating the particle in a non-aqueous solution of the active ingredient.

In another embodiment, the active ingredient is mixed with an adhesive before application to a particle. An adhesive is a substance that binds to a particle, such that the active ingredient adheres to the particle in suspension in the adhesive. The adhesive may be the same as the binder or different. The choice of adhesive depends on the particle components and will be evident to one skilled in the art. Examples of adhesives include, but are not limited to, substances listed herein as binder components. Preferably, the adhesive is calcium lignosulfonate, molasses, a liquid corn starch, a liquid corn syrup, bentonite clay or a combination of these.

For example, the active ingredient in powdered form is adhered to the outside surface of the particle with the use of an adhesive. An adhesive liquid may be used and is applied before or after the addition of the powdered active ingredient or it may be applied at the same time as the active ingredient. The choice of adhesive depends on the particle components and will be evident to one skilled in the art. Examples of a liquid adhesive include but are not limited to binders listed herein, including mineral oils or polymer liquids such as polybutene.

Durability of Particles

The particles of the present invention have a minimum Resistance To Attrition (RTA) rating ranging from 60% to 100% as determined by the method detailed in Example R or an art-recognized equivalent procedure.

Size of Particles

The particles of the present invention have a mean particle domain size that ranges from 0.1 millimeter to 30 millimeters. More preferably, the mean particle domain size ranges from 0.25 millimeter to 20 millimeters. Still more preferably, the mean particle domain size ranges from 0.50 millimeter to 15 millimeters. The particles formed by the process of the present invention have a Uniformity Index rating in the range of 30 to 60 where the Uniformity Index rating is calculated as the $10^{th}$ percentile particle size expressed as a percentage of the $95^{th}$ percentile particle size.

Shape of the Particles

Particles of the present invention take any shape illustratively including spheres, cylinders, ellipses, rods, cones, discs, needles and irregular. In a preferred embodiment the particles are approximately spherical.

Method of Use

The particles of the present invention are administered to a target to produce a desired effect on a desirable or an undesirable organism. Particles are administered by a method that delivers the nitrogen-containing ingredient to the vicinity of a desirable organism whose health is to be encouraged. Further, the particles are administered by a method that delivers the active ingredient to an area where it will be available to a targeted desirable or undesirable organism. For example, where a particle contains a controlled release nitrogen source such as methylene urea oligomers and an active ingredient such as a plant hormone, the particles are delivered to a desirable plant target, such as a golf course lawn, by broadcast scattering via rotary spreader. The particles are then dispersed by water that is user applied or natural such as rain, dew or atmospheric humidity.

Alternatively, the particles are placed in a limited target area such as near a particular desired plant in a garden or in a crop row. In another embodiment, the particles are placed under the soil surface.

A target desirable organism illustratively includes cultivated plants such as lawn grass, crops, flowers, shrubs, trees and bushes. Target undesirable organisms illustratively include pest insects at any stage of development, bacteria, molds, algaes, weeds, worms and rodents.

EXAMPLES

Example A

Dispersible Potash: Using a pan agglomeration disk, a binder such as calcium lignosulfanate, corn starch, and corn syrup is applied to a mixture of water-dispersible potassium source of organic origin fines (material less than 250 microns). The agglomeration disk is operated and adjusted to generate the desired size distribution of particles before the particles are conveyed to a fluid bed drier where the material is dried at a temperature of 140° F. to a moisture content of less than 0.5%. The material is then separated into various size categories using conventional gyroscopic screeners. General size of these product streams are as follows: 3,360 microns and larger, from 3,360 microns to 1,191 microns, from 1,191 microns to 594 microns, and material smaller than 594 microns. The range of sizing for each product stream can be varied to separate the desired material from the mixture of sizing.

Example B

Dispersible Potash Containing Pesticides (Powdered Pesticides): A mixture of water-dispersible potash fines and a powdered pesticide (such as PCMB, Prodiamine, or Thiphanate-Methyl) is added to a pan agglomeration disk. A binder such as calcium lignosulfanate, corn starch, bentonite clay, or corn syrup is sprayed onto the mixture. The pan agglomeration disk is operated and adjusted to provide the desired size distribution of particles. The material is then conveyed to a fluid bed drier where the material is dried at a temperature of 140° F. to a moisture content of less than 0.5%. The material is then separated into various size categories using conventional gyroscopic screeners. General size of these product streams are as follows: 3,360 microns and larger, from 3,360 microns to 1,191 microns, from 1,191 microns to 594 microns, and material smaller than 594 microns. The range of sizing for each product stream can be varied to separate the desired material from the mixture of sizing.

Example C

Dispersible Potash Containing Pesticides such as liquid pesticides: Using a pan agglomeration disk, a liquid pesticide and a binder such as calcium lignosulfanate, corn starch, and corn syrup was applied to a mixture of water-dispersible potash fines (material less than 250 microns). The agglomeration disk is operated and adjusted to generate the desired size distribution of particles before the particles are conveyed to a fluid bed drier where the material was dried at a temperature of 140° F. to a moisture content of less that 0.5%. The material is then separated into various size categories using conventional gyroscopic screeners. General size of these product streams are as follows: 3,360 microns and larger, from 3,360 microns to 1,191 microns, from 1,191 microns to 594 microns, and material smaller than 594 microns. The range of sizing for each product stream can be varied to separate the desired material from the mixture of sizing.

Example D

Dispersible Potash with Other Nutrient Sources, Micronutrients, Soil Amendments, or Biostimulants: Using a pan agglomeration disk, a binder such as calcium lignosulfanate, corn starch, bentonite clay and corn syrup is applied to a mixture of water-dispersible potash fines, other nutrient sources (diammonium phosphate or sulfate of potash for example), micronutrients (such as iron sulfate or manganese oxide), soil amendments (such as humic acid materials), or biostimulants with all materials less than 250 microns in size. The agglomeration disk is operated and adjusted to generate the desired size distribution of particles before the larger particles were conveyed to a fluid bed drier where the material was dried at a temperature of 140° F. to a moisture content of less that 0.5%. The material is then separated into various size categories using conventional gyroscopic screeners, General size of these product streams are as follows: 3,360 microns and larger, from 3,360 microns to 1,191 microns, from 1,191 microns to 594 microns, and material smaller than 594 microns. The range of sizing for each product stream can be varied to separate the desired material from the mixture of sizing.

Example E

Dispersible Potash with Other Nutrient Sources, Micronutrients, Soil Amendments, or Biostimulants Containing Pesticides such as powdered pesticides: A mixture of potash fines, other nutrient sources (methylene urea for example), micronutrients (such as iron sulfate or manganese oxide), soil amendments (such as humic acid materials), or biostimulants and a powdered pesticide (such as PCNB, Prodiamine, or Thiphanate-Methyl) is added to a pan agglomeration disk, A binder such as calcium lignosulfanate, corn starch, bentonite clay, or corn syrup is sprayed onto the mixture. The pan agglomeration disk is operated and adjusted to provide the desired size distribution of particles. The material is then conveyed to a fluid bed drier where the material is dried at a temperature of 140° F. to a moisture content of less than 0.5%. The material is then separated into various size categories using conventional gyroscopic screeners. General size of these product streams were as follows: 3,360 microns and larger, from 3,360 microns to 1,191 microns, from 1,191 microns to 594 microns, and material smaller than 594 microns. The range of sizing for each product stream can be varied to separate the desired material from the mixture of sizing.

Example F

Dispersible Potash with Other Nutrient Sources, Micronutrients, Soil Amendments, or Biostimulants Containing Pesticides such as liquid pesticides: Using a pan agglomeration disk, a liquid pesticide and a binder such as calcium lignosulfanate, corn starch, bentonite clay, or corn syrup are applied to a mixture of water-dispersible potash fines, other nutrient sources (isobutylidene diurea for example), micronutrients (such as iron sulfate or manganese oxide), soil amendments (such as humic acid materials), or biostimulants, with all material less than 250 microns in diameter. The agglomeration disk is operated and adjusted to generate the desired size distribution of particles before the particles are conveyed to a fluid bed drier where the material was dried at a temperature of 140° F. to a moisture content of less that 0.5%. The material is then separated into various size categories using conventional gyroscopic screeners. General size of these product streams were as follows: 3,360 microns and larger, from 3,360 microns to 1,191 microns, from 1,191 microns to 594 microns, and material smaller than 594 microns. The range of sizing for each product stream can be varied to separate the desired material from the mixture of sizing.

Example G

Post Production Surface Coating of Dispersible Potash (Example A) or Dispersible Potash Containing Other Nutrient Sources, Micronutrients, Soil Amendments, or Biostimulants (Example D) with a Powdered Pesticide. Materials generated by the methods described in Example A or Example D above, are fed to a blender (such as a Forberg fluidized zone blender) or other coating equipment (such as a coating drum). The material is sprayed with a liquid, such as a light weight mineral oil, to make the surface slightly tacky before adding a powdered pesticide (such as Prodiamine, Thiophanate-Methyl, or PCNB). A second spray of liquid may be necessary to adhere the powder to the surface of the material.

Example H

Post Production Surface Impregnation of Dispersible Potash (Example A) or Dispersible Potash Containing Other Nutrient Sources, Micronutrients, Soil Amendments, or Biostimulants (Example D) with a Liquid Pesticide. Materials generated by the methods described in Example A or Example D above, are fed to a blender (such as a Forberg fluidized zone blender) or other coating equipment (such as a coating drum). The material is then sprayed with a liquid pesticide that slightly penetrates the surface of the material. The material is mixed to assure even distribution of the pesticide to all particles.

Example I

Water-dispersible sulfate or phosphate of potash particles are generated in an exemplary method, using an 18" agglomeration pan and a fluid bed drier.

An illustrative procedure for producing a small batch of particles:

1. 500-1000 grams of sulfate or phosphate of potash particles fines passing 50 mesh are weighed out.
2. The ratio of sulfate or phosphate of potash fines to binder material depends on the binder and varies from about 19:1 to about 1:3. Preferably the ratio of sulfate or phosphate of potash fines to binder is in the range from 10:1 to 1:1. More preferably the ratio of sulfate or phosphate of potash fines to binder is in the range from 7:1 to 2:1.
3. Approximately ⅔ of this material is placed into the 18" agglomeration pan and the speed of rotation and the slope of incline of the pan are adjusted to ensure an acceptable falling curtain of material in the pan bed.
4. A binder is applied via a spray bottle, peristaltic pump with air atomizing nozzle, or sparge tube depending on the material used. Binder is added by the operator until particle growth begins to occur.
5. As necessary, the size of the particles is adjusted by the operator by crushing the material back down by hand as the material is rotating within the pan.
6. The additional ⅓ of the sulfate or phosphate of potash fines is added in small amounts to the pan along with additional binder as needed.
7. After all of the sulfate or phosphate of potash is added to the pan and any binder required to grow the particles is applied, the material is discharged into a collection container and transported to a fluid bed drier.
8. The material is placed in a fluid bed drier to drive off moisture added by the binder material. The temperature of the air entering the drier varies depending on the materials included in the particles.
9. The material is dried until the temperature of the air exiting the drier stabilizes for a period of five minutes.
10. Once the material is taken from the drier, it is split into size fractions using round sieve screens by hand. For example, four fractions are used including: +6 mesh (overs), −6/+16 mesh (coarse), −16/+30 mesh (greens), and −30 mesh (fines).
11. The size fractions are placed into an oven and dried for additional period. For example, the particles are placed at a temperature ranging from 70° F. to 150° F. for 1 hour to 48 hours. More preferably the temperature ranges from 90° F. to 120° F. for 1 hour to 48 hours. In a specific example, the particles are dried at 110° F. for an additional 16+ hours.
12. When pulled from the oven, the size fractions are checked for dispersibility and resistance to attrition.

Example J

An example procedure for making particles using Norlig A-Lignin as a binder is as follows:

500 g sulfate or phosphate of potash fines, −50 mesh, are combined with 118.8 g of Norlig A/Water mixture (10:1) using a peristaltic pump/air atomizing nozzle. Drier inlet air is used at 190° F. Final drier exiting air has a temperature of 164° F.

Assay of dispersibility of particles is acceptable and Resistance to Attrition is 95.6%.

Example K

An example procedure for making particles using Cerestar Corn Starch as a binder is as follows:

500 g sulfate or phosphate of potash fines, −50 mesh are combined with 158.3 g of Cerestar Corn Starch using a peristaltic pump/air atomizing nozzle. Drier inlet air is used at 140° F. Final drier exiting air has a temperature of 117° F.

Assay of dispersibility of particles is acceptable and Resistance to Attrition is 94.8%.

Example L

An example procedure for making particles using corn syrup as a binder is as follows:

500 g sulfate or phosphate of potash fines, −50 mesh, are combined with 157.4 g of corn syrup/water (5:1) using a peristaltic pump/air atomizing nozzle. Drier inlet air is used at 140° F. Final drier exiting air has a temperature of 117° F.

Assay of dispersibility of particles is acceptable and Resistance to Attrition is 96.1%.

Example M

An example procedure for making particles using Norlig A-Lignin as a binder is as follows:

1000 g sulfate or phosphate of potash fines, −50 mesh, are combined with 240 g of Norlig A/Water mixture (10:1) using a peristaltic pump/air atomizing nozzle. Drier inlet air is used at 190° F. Final drier exiting air has a temperature of 164° F.

Assay of dispersibility of particles is acceptable and Resistance to Attrition is 94.5%.

Example N

An example procedure for making particles coated with a powdered active ingredient is as follows:

Particles are generated as outlined in Example I. When dry, 1000 grams of the selected size fraction of finished particles are placed in a blender. 40 grams of the powdered active ingredient is added to the blender, which is then turned on. After 30 seconds of blending, the adhesive liquid is added to the blender. A total of 20 grams of adhesive liquid is added over 1 minute, which is followed by an additional 1 minute of blending. The material is then discharged from the blender.

Example O

Resistance to Attrition Determination

Apparatus: Ro-Tap sieve shaker with 8-inch sieves, balance with 0.1 g sensitivity, 10-min timer, and 10 steel balls with smooth surfaces and 16 mm (⅝ in.) in diameter.

1) Using information from the Screen Analysis, choose your limiting screen size. The following table indicates the limiting screen for several fertilizer blends.

| Fertilizer Sizing | U.S. (Tyler) |
| --- | --- |
| Coarse | 16 (14) |
| Premium Standard | 20 (20) |
| Fairways | 20 (20) |
| Greens | 30 (28) |

2) Place about 75 g of a representative sample onto the limiting screen.
3) Reassemble the screen apparatus with the limiting screen just above the pan.
4) Place the screen apparatus onto the shaker and run it for 10 min (Use the hammer).
5) Empty the pan. Transfer 50.0 g of sample to the pan.
6) Put ten (10) 16-mm steel balls in the pan with the sample.
7) Reassemble the screen apparatus and place it onto the shaker and run it for 10 min (Do not use the hammer).
8) Remove the steel balls from the pan and transfer the sample back into the limiting screen.
9) Place the screen apparatus back onto the shaker and run it for 10 min (Use the hammer).
10) Weigh out the amount that remained on the limiting screen to the nearest 0.1 g and compare it to the original amount.

Percent resistance to attrition=$\{(100 \cdot a)/b\}$, where a is the weight of the fraction that remained on the limiting screen in Step 10 and b is total weight of the sample in Step 5.

Example P

The process of Example A is repeated with white oak ash fines as the potash source (less than 250 microns) to obtain like pellets to Example A.

Example Q

The process of Example F is repeated with white oak ash fines as the potash source (less than 250 microns) to obtain like pellets to Example F.

Example R

The process of Example G is repeated with the pellets to Example P in lieu of Example A to obtain like pellets to those of Example G.

Any patents or publications mentioned in this specification are indicative of the level of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A plurality of water-dispersible particles comprising: an organic origin potash present in an amount ranging from 5% to 99% by weight of the total dry weight of the plurality of particles and having a mean aggregate size of less than 250 micrometers; and
   a binder component, present in an amount ranging from 1% to 95% by weight of the total dry weight of the plurality of particles, the particles having a mean particle domain size;
   the organic origin potash and the binder component present in a form such that contact with water causes particle dispersion into more than 100 pieces wherein the particle dispersion occurs within one hour of water contact;
   wherein the organic origin potash is selected from a first group consisting of kali vinesse, seaweed, cellulosic products, and ashes formed from said first group; and
   wherein the binder component is selected from a second group consisting of carbohydrates, proteins, lipids, synthetic organic polymers, glycolipids, glycoproteins, lipoproteins, lignins, a lignin derivative, a carbohydrate-based composition, and combinations thereof.

2. The plurality of water-dispersible particles of claim 1 further comprising an active ingredient.

3. The plurality of water-dispersible particles of claim 1 wherein the organic origin potash is present in an amount ranging from 30% to 99.5% by weight of the total dry weight of the particles.

4. The plurality of water-dispersible particles of claim 1 wherein the binder component is present in an amount ranging from 5% to 75% by weight of the total dry weight of the particles.

5. The plurality of water-dispersible particles of claim 1 wherein the binder component further comprises a clay.

6. The plurality of water-dispersible particles of claim 1 further comprising an adhesive.

7. The plurality of water-dispersible particles of claim 2 wherein the active ingredient is selected from the group consisting of: a fertilizer, a soil nutrient, an amendment material, and a combination thereof.

8. The plurality of water-dispersible particles of claim 7 wherein the active ingredient is a fertilizer and is selected from the group consisting of: urea, methylene urea, sulfur coated urea, isobutylidene diurea, ammonium nitrate, ammonium sulfate, ammonium phosphate, triple super phosphate, phosphoric acid, potassium sulphate, potassium nitrate, potassium metaphosphate, potassium chloride, dipotassium carbonate, potassium oxide and a combination thereof.

9. The plurality of water-dispersible particles of claim 7 wherein the active ingredient is a soil nutrient selected from the group consisting of: calcium, magnesium, sulfur, iron, manganese, copper, zinc; oxides thereof; salts thereof, and a combination thereof.

10. The plurality of water-dispersible particles of claim 7 wherein the amendment material is a natural organic product.

11. The plurality of water-dispersible particles of claim 10 wherein the active ingredient is a natural organic product selected from the group consisting of: humic acid, blood meal, bone meal, seed meal, feather meal, soy meal, meat meal, animal waste, activated sludge, hydrolyzed animal hair, a fish byproduct, chitin, composts and combinations thereof.

12. The plurality of water-dispersible particles of claim 2 wherein the active ingredient is selected from the group consisting of a biological factor and a biostimulant.

13. The plurality of water-dispersible particles of claim 12 wherein the biological factor is selected from the group consisting of: an algicide, a bacteriocide, a defoliant, a desiccant, a fungicide, an herbicide, an insecticide, an insect growth regulator, a miticide, a nematicide, an ovicide, a pesticide, a pheromone, a repellent and a rodenticide, and a combination thereof.

14. The plurality of water-dispersible particles of claim 12 wherein the biostimulant is selected from the group consisting of a plant growth hormone and a plant growth regulator, and a combination thereof.

15. The plurality of water-dispersible particles of claim 12 wherein the biostimulant is selected from the group consisting of: a cytokinin, an auxin, a gibberellin, ethylene and absisic acid, and a combination thereof.

16. The plurality of water-dispersible particles of claim 1 wherein water causes particle dispersion of each of the particles into between 1,000 and 10,000 pieces.

17. The plurality of water-dispersible particles of claim 1 wherein the mean particle domain size ranges from 0.1 millimeter to 30 millimeters.

* * * * *